United States Patent [19]

Gregorio

[11] Patent Number: 5,346,475
[45] Date of Patent: Sep. 13, 1994

[54] SINGLE USE SYRINGE

[76] Inventor: Edward Gregorio, 9 Van Doren Ave., Chatham, N.J. 07928

[21] Appl. No.: 144,882

[22] Filed: Oct. 27, 1993

[51] Int. Cl.$^5$ .............................................. A61M 5/00
[52] U.S. Cl. ................................... 604/110; 604/198
[58] Field of Search ............... 604/110, 198, 218, 227, 604/263

[56] References Cited

U.S. PATENT DOCUMENTS

| | | | |
|---|---|---|---|
| 1,019,465 | 3/1912 | Chatfield, Jr. | 604/227 X |
| 4,752,290 | 6/1988 | Schramm | 604/198 |
| 5,057,079 | 10/1991 | Tiemann et al. | 604/110 |
| 5,195,993 | 3/1993 | Gianakos | 604/198 X |

Primary Examiner—John D. Yasko
Attorney, Agent, or Firm—Richard T. Laughlin

[57] ABSTRACT

A single-use syringe for covering its needle after injection of a medical preparation. The syringe has a barrel and has a non-reversible shield for covering the needle. The shield has an inclined interior shield tooth of resilient material, and the barrel has a coacting inclined exterior row of teeth of non-resilient material, whereby the shield tooth locks behind a barrel tooth when the needle is covered and the shield cannot reverse its travel.

3 Claims, 1 Drawing Sheet

SINGLE USE SYRINGE

FIELD OF THE INVENTION

The invention generally relates to a single use syringe and, in particular, the invention relates to a single use syringe having a shield with a non-reversible rack and spring tooth lock subassembly.

BACKGROUND OF THE INVENTION

Persons in the medical practice, i.e., doctors, nurses and laboratory technicians, are exposed to hypodermic needles which have been used for the injection or withdrawal of fluids into or from persons having various illnesses. Many diseases can be contracted this way, and the present danger of contracting Hepatitis B, Acquired Immune Deficiency Syndrome (AIDS) and other diseases causes a need for extra caution on the part of those health professionals. A used hypodermic syringe needle is a hazard of which the health profession has become more aware since the fairly widespread distribution of these virulent strains. Thus, there is a need to protect health professionals against being scratched or punctured by those needles.

The prior art syringe is described in U.S. Pat. Nos. 5,120,309 and 5,154,698. The prior art syringe includes a barrel having an axis and having a coaxial end wall needle and having a coaxial plunger, a protective shield slidably engaging and mounted on the barrel for covering the needle in one shield position after injecting medication, or for exposing the needle in a second exposed position before injecting medication, and a detent subassembly for temporarily holding the shield in either position.

One problem with the prior art syringe is that the used needle tip is covered by a reversible shield after injecting medication, which can lead to a needle puncture that can cause serious harm.

SUMMARY OF THE INVENTION

According to the present invention, a syringe with a non-reversible shield is provided. This syringe comprises a barrel having an axis and having an end wall needle and having a coaxial plunger, a protective shield slidably engaged and mounted on the barrel for covering the needle after needle use, and a non-reversible lock subassembly for locking the shield in place after covering the needle. The protective shield has finger grips to aid in administration.

By using the shield having a non-reversible lock subassembly, the danger of serious harm from a puncture from a used needle is minimized.

One object of the present invention is to minimize the danger of serious harm from a puncture from a used needle.

Another object is to provide a syringe having a protective shield with a non-reversible lock subassembly, so that the shield always protects the used syringe needle to prevent accidental harm therefrom.

A further object is to provide a syringe having a protective shield with an automatic non-reversible lock subassembly which does not require a driven rivet, or the like, for locking.

BRIEF DESCRIPTION OF THE DRAWINGS

The foregoing and other objects, features and advantages will be apparent from the following description of the preferred embodiment of the invention as illustrated in the accompanying drawings.

DESCRIPTION OF THE PREFERRED EMBODIMENT

Figure 1:
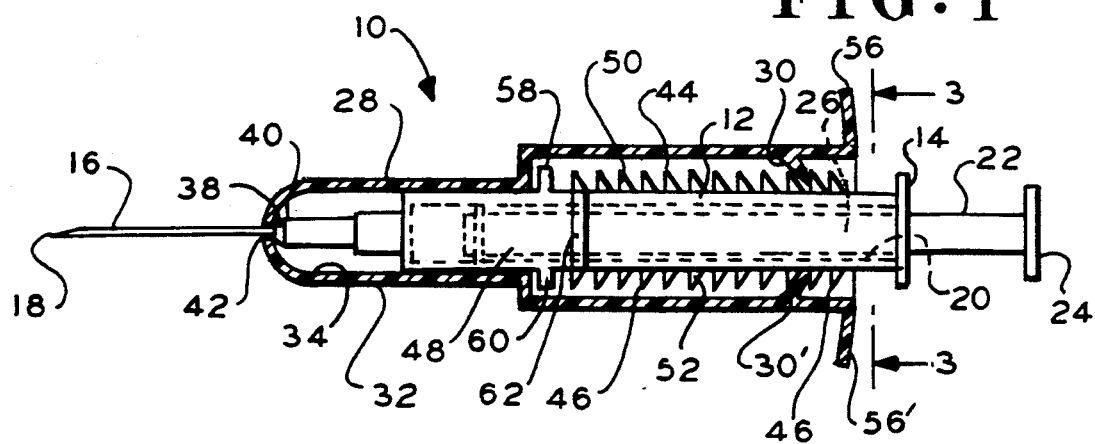
FIG. 1 is a plan view of a syringe according to the present invention showing the cover in its open position with the needle exposed.

Hypodermic syringe 10 is a standard medical hypodermic syringe. It has a barrel 12 which carries finger flange 14 on the rear end thereof and a hypodermic needle 16 at the front end thereof. The needle has a sharp tip 18. The syringe has a bore 20 therein which is in fluid communication with the passage through the needle to the tip of the needle. Hypodermic plunger 22 is slidable within the bore. The plunger carries a thumb pad 24 on the outer end and a piston 26 on the inner end thereof. The piston is in slidable but sealing relation with respect to the bore so that, when the thumb is used to press the plunger forward into the barrel, the contents of the barrel forward of the plunger are expelled through the needle. Such a structure is commonly used for injecting medication into a patient. The problem is protecting the sharp tip 18 of the hypodermic needle after it has been used.

Protective shield 28 provides this protection, and its locks 30 and 30' aid in the control of the protective shield along the length of the barrel of the hypodermic syringe. Protective shield 28 has a generally cylindrical exterior surface 32 and a generally cylindrical interior surface 34 coaxial therewith to define a thin-walled tube. The interior diameter is such as to slidably receive the barrel 12 of the syringe 10. Shield 28 is provided with a flange or handles 56, 56' for gripping with the finger at its near end and a hemispherical closure 38 at its far end. The closure 38 is provided with a cylindrical boss 40 which has a needle opening 42 therethrough. The hemispherical closure, boss 40 and needle opening 42 are substantially coaxial with the surfaces of the protective shield. The needle opening is in alignment with needle 16. The length of the shield is such that, when it is in its forward position, shown in FIG. 1, the needle is fully-enclosed by protective shield 28.

Figure 2:
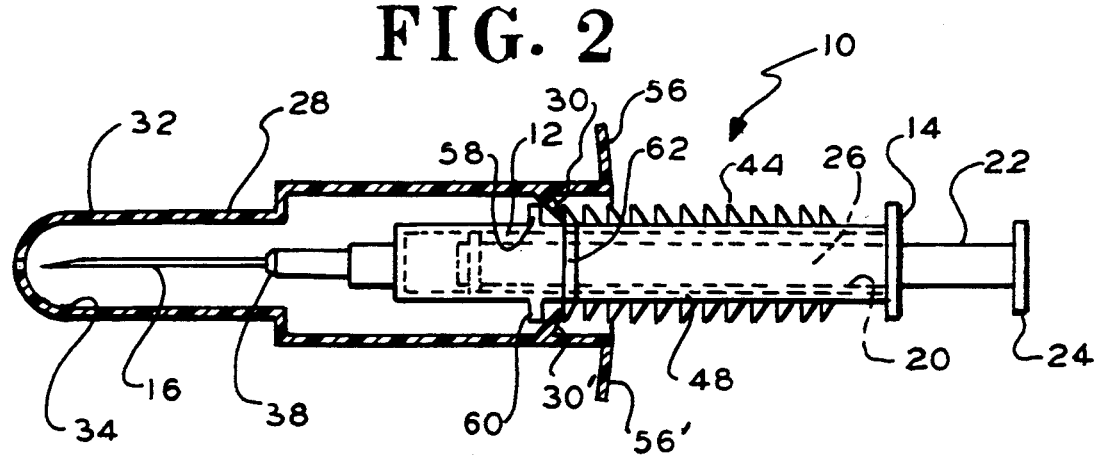
FIG. 2 is a plan view of a syringe according to the present invention showing the cover in its closed position with the needle covered.
Figure 3:
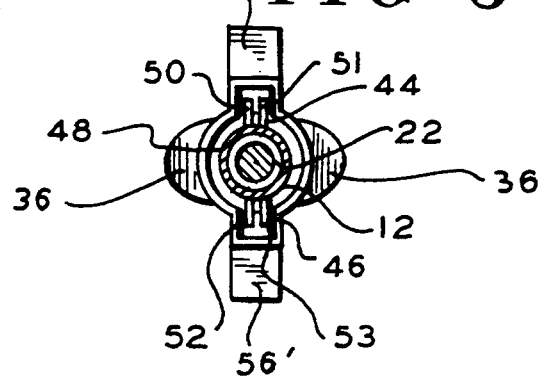
FIG. 3 is a section view as taken along the line 3—3 of FIG. 1.

As shown in FIGS. 1 through 3, according to the invention, locks 30 and 30' are provided. Locks 30 and 31' have diametrically opposite upper and lower lock subassemblies 44, 46. Subassembly 44 is substantially identical in construction to subassembly 46. Subassembly 44 has upper barrel teeth 50, 51, which are arranged in two rows and which are fixedly connected to barrel outer surface 48. Subassembly 46 has corresponding lower barrel teeth 52, 53 which are fixedly connected to shield interior surface 34. There are twelve barrel teeth 50 or 51 or 52 or 53 in each row. Locks 30 and 30' are each made of resilient, spring-like material.

Subassemblies 44, 46 respectively have upper and lower central barrel stop members 58, 60. The stop members hit locks 30, 30' limiting forward travel of shield 28, and locking the shield teeth.

Barrel teeth 50, 51, 52, 53 are inclined in a forward direction allowing locks 30, 30' to slid until they meet stops 50, 60 causing the shield to be locked in a closed position. A bar or bridge 62 can be used which can have a convex surface to maintain the cover in a spaced relation from the syringe.

The advantages of syringe 10 are indicated hereafter:

A) Syringe 10 can avoid a needle puncture after injecting a medication and avoid serious harm therefrom.
B) Syringe 10 has a protective shield 28 with an automatic non-reversible lock unit 40 for protecting against a used needle and accidental harm therefrom.
C) Syringe 10 avoids the need for lock rivets, or the like, which require locking tools.
D) Syringe 10 minimizes the extent and time for handling the used needle before shielding.

While the invention has been described in its preferred embodiment, it is to be understood that the words which have been used are words of description rather than limitation and that changes may be made within the purview of the appended claims without departing from the true scope and spirit of the invention in its broader aspects.

What is claimed is:

1. A single use syringe comprising:

a barrel having an axis and having an end needle and having a coaxial plunger;

a protective shield slidably engaging and supported on the barrel for covering the needle after needle use; and a non-reversible lock unit for locking the shield in place to the barrel after covering the needle wherein the lock unit includes at least one lock subassembly comprising:

at least one axial parallel row of barrel teeth fixedly connected to the barrel at an outer surface of the barrel; and at least one shield tooth fixedly connected to the shield at an interior surface thereof;

said shield tooth being a resilient spring-like tooth and being inclined in a rearward direction away from the needle for locking in front of a tooth at the front of the row of barrel teeth when the shield is in a needle-covering position, wherein the shield has a slot disposed parallel to the axis for travel therethrough of the row of barrel teeth;

the shield has a bubble-like wall extension disposed over and covering over the slot; and a bar is provided on the barrel to maintain the cover in a spaced relationship between the barrel and the cover.

2. The syringe of claim 1, wherein a curved flange is affixed to the outer surface of the protective shield for gripping during use.

3. The syringe of claim 1, wherein the barrel has a stop member disposed near the front of the row of barrel teeth and peripherally spaced therefrom; and the shield has a stop member disposed near the rear of the shield for hitting the barrel stop member and stopping travel of the shield after covering the needle.

* * * * *